United States Patent [19]

Balli et al.

[11] 4,174,856
[45] Nov. 20, 1979

[54] CHROMENOINDOLE COLOR FORMERS

[75] Inventors: Heinz Balli, Riehen; Sigmund Gunzenhauser, Arlesheim; Jean C. Petitpierre, Kaiseraugst, all of Switzerland

[73] Assignee: Ciba-Geigy Corporation, Ardsley, N.Y.

[21] Appl. No.: 935,393

[22] Filed: Aug. 21, 1978

Related U.S. Application Data

[62] Division of Ser. No. 799,063, May 20, 1977, Pat. No. 4,123,439.

[30] Foreign Application Priority Data

Jun. 4, 1976 [CH] Switzerland .................. 7115/76

[51] Int. Cl.² ............................ B41M 5/22
[52] U.S. Cl. .................... 282/27.5; 106/21; 427/151; 428/307; 428/913; 428/914
[58] Field of Search ............ 106/21, 288 Q; 282/27.5; 260/326.5 B, 293.58; 427/151; 428/307, 411, 537, 913, 914; 544/81, 142

[56] References Cited

U.S. PATENT DOCUMENTS 3,929,829  12/1975  Borror .................. 96/3 X

*Primary Examiner*—George F. Lesmes
*Assistant Examiner*—Bruce H. Hess
*Attorney, Agent, or Firm*—Prabodh I. Almaula

[57] ABSTRACT

A chromenoindole compound of the formula

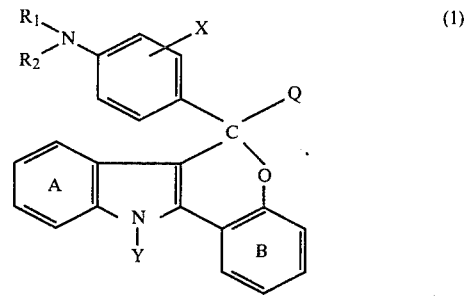

wherein $R_1$ and $R_2$ independently of one another represent hydrogen, alkyl which has at most 12 carbon atoms and is unsubstituted or substituted by halogen, hydroxyl, cyano or lower alkoxy; cycloalkyl, phenyl, benzyl, or phenyl or benzyl which are substituted by halogen, lower alkyl or lower alkoxy, or $R_1$ and $R_2$, together with the nitrogen atom which links them, represent a 5-membered or 6-membered heterocyclic radical, Q is hydrogen, lower alkyl, phenyl, benzyl or the groups of the formulae (1a) or (1b)

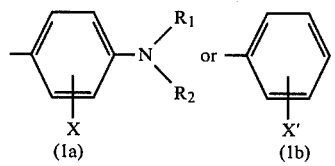

X and X' each represent hydrogen, halogen, lower alkyl or lower alkoxy, Y represents hydrogen, alkyl of 1 to 12 carbon atoms, phenyl or benzyl and the rings A and B independently of one another are unsubstituted or substituted by halogen, nitro, lower alkyl, lower alkoxy, phenoxy, amino or amino substituted by lower alkyl, phenyl or benzyl; these compounds are particularly useful as color formers which give intense red to blue color shades of excellent light fastness when they are brought into contact with an electron acceptor.

14 Claims, No Drawings

CHROMENOINDOLE COLOR FORMERS

This is a division of application Ser. No. 799,063 filed on May 20, 1977, now U.S. Pat. No. 4,123,439.

The present invention relates to new chromenoindole compounds, processes for their manufacture and their use as colour-forming agents in pressure-sensitive or heat-sensitive recording materials.

The new chromenoindole compounds correspond to the general formula

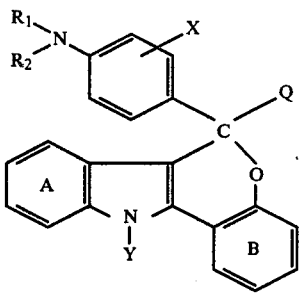

(1)

in which $R_1$ and $R_2$ independently of one another denote hydrogen, alkyl which has at most 12 carbon atoms and is unsubstituted or substituted by halogen, hydroxyl, cyano or lower alkoxy, cycloalkyl, phenyl, benzyl, or phenyl or benzyl which are substituted by halogen, lower alkyl or lower alkoxy, or $R_1$ and $R_2$, together with the nitrogen atom which links them, denote a 5-membered or 6-membered, preferably saturated, heterocyclic radical, Q denotes hydrogen, lower alkyl, benzyl or the groups of the formulae (1a) or (1b)

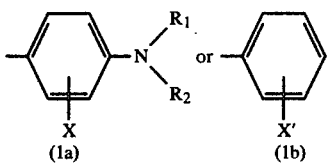

X and X' each denote hydrogen, halogen, lower alkyl or lower alkoxy, Y denotes hydrogen, alkyl with 1 to 12 carbon atoms, phenyl or benzyl and the rings A and B independently of one another can be further substituted by halogen, nitro, lower alkyl, lower alkoxy, phenoxy or an amino group which is optionally substituted by lower alkyl, phenyl or benzyl.

In the definition of the radicals of the chromenoindole compounds, lower alkyl and lower alkoxy as a rule represent those groups which contain 1 to 5, and especially 1 to 3, carbon atoms, such as, for example, methyl, ethyl, n-propyl, isopropyl, n-butyl, sec.-butyl, tert.-butyl or amyl and methoxy, ethoxy or isopropoxy.

If the substituents $R_1$, $R_2$ and Y represent alkyl groups, these can be straight-chain or branched alkyl radicals. Examples of such alkyl radicals are methyl, ethyl, n-propyl, isopropyl, n-butyl, sec.-butyl, n-hexyl, n-octyl or n-dodecyl.

If the alkyl radicals in $R_1$ and $R_2$ are substituted, they are, above all, cyanoalkyl, halogenoalkyl, hydroxyalkyl or alkoxyalkyl, each with 2 to 4 carbon atoms, such as, for example, β-cyanoethyl, β-chloroethyl, β-hydroxyethyl, β-methoxyethyl or β-ethoxyethyl.

Examples of cycloalkyl in the meaning of the R radicals are cyclopentyl or, preferably, cyclohexyl.

Preferred substituents in the benzyl and phenyl groups of the R radicals are, for example, halogens, methyl or methoxy. Examples of araliphatic and aromatic radicals of this type are p-methylbenzyl, o- or p-chlorobenzyl, o- or p-tolyl, xylyl, o-, m- or p-chlorophenyl or o- or p-methoxyphenyl.

If the substituents $R_1$ and $R_2$, together with the common nitrogen atom, represent a heterocyclic radical, this is, for example, pyrrolidino, piperidino, pipecolino, morpholino, thiomorpholino or piperazino.

The substituents $R_1$ and $R_2$ are preferably benzyl or lower alkyl. The N-substituent Y is, in particular, hydrogen, phenyl, benzyl or alkyl with 1 to 8 carbon atoms, for example n-octyl or, above all, methyl or ethyl.

The radical Q advantageously denotes the group (1a). X and X' are preferably hydrogen or also halogen, methyl, methoxy or ethoxy.

The rings A and B are preferably not further substituted or independently of one another are further substituted by halogen, lower alkyl or lower alkoxy, for example by chlorine, methyl, tert.-butyl or methoxy. The ring B can also carry an amino group which is optionally substituted by lower alkyl, especially by methyl or ethyl.

Colour-forming agents which are important in practice, amongst the chromenoindole compounds of the formula (1) correspond to the general formula

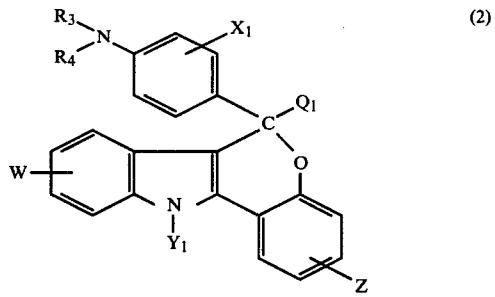

(2)

in which $R_3$ and $R_4$ independently of one another denote lower alkyl, phenyl or benzyl and $R_3$ also denotes hydrogen, or $R_3$ and $R_4$, together with the nitrogen atom which links them, denote a pyrrolidino, piperidino or morpholino radical, $X_1$ denotes hydrogen, halogen, methyl or lower alkoxy, $Q_1$ denotes hydrogen, lower alkyl, phenyl, benzyl or the group of the formula

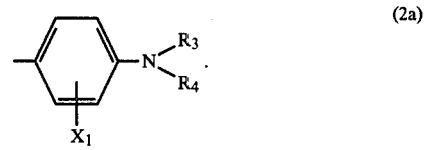

(2a)

W denotes hydrogen, halogen, lower alkyl, lower alkoxy or phenoxy, $Y_1$ denotes hydrogen, lower alkyl, phenyl or benzyl and Z denotes hydrogen, halogen, lower alkyl, lower alkoxy or an amino group which is optionally substituted by lower alkyl, benzyl or phenyl.

In connection with the above substituents in formulae (1) and (2), halogen is, for example, fluorine, bromine or, preferably, chlorine.

Chromenoindole compounds of the general formula

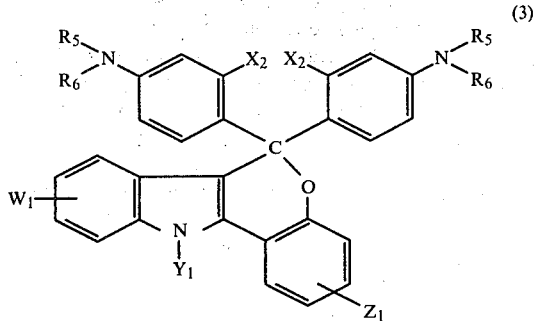

(3)

in which $R_5$ and $R_6$ independently of one another denote lower alkyl or benzyl, $W_1$ denotes hydrogen, chlorine, methyl or methoxy, $X_2$ denotes hydrogen, methyl, methoxy or ethoxy, $Y_1$ denotes hydrogen, lower alkyl, benzyl or phenyl and $Z_1$ denotes hydrogen, chlorine, methyl, methoxy or an amino group which is monosubstituted or disubstituted by lower alkyl are of very particular interest. In this formula, $Z_1$ preferably denotes hydrogen, chlorine or methyl.

Amongst these compounds of the formula (3), those in which $R_5$ and $R_6$ denote methyl or ethyl, $X_2$ denotes hydrogen, methyl or ethoxy, $W_1$ and $Z_1$ each denote hydrogen and $Y_1$ denotes hydrogen, methyl or ethyl are particularly preferred.

The chromenoindole compounds according to the invention are manufactured by reacting a 2-(2'-hydroxyphenyl)-indole compound of the general formula

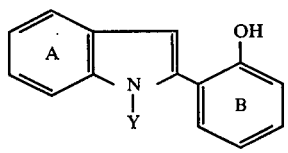

(4)

with a keto compound of the general formula

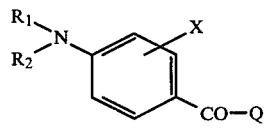

(5)

in which A, B, Y, $R_1$, $R_2$, X and Q have the indicated meaning.

The reaction is preferably carried out by bringing the reactants to reaction in the presence of an acid dehydrating agent. Examples of condensing agents of this type are sulphuric acid, oleum, phosphorus pentoxide or, preferably, acid halides.

Acid halides which can be used are acid bromides or, preferably, acid chlorides of phosphorous acid or sulphurous acid, of phosphoric acid, of sulphuric acid or of carbonic acid or oxalic acid. Oxalyl chloride, oxalyl bromide, thionyl chloride, sulphuryl chloride, phosphorus trichloride, phosphorus tribromide or, preferably, phosgene or in particular phosphorus oxychloride are advantageously used.

The reaction of the indole compound of the formula (4) with the keto compound of the formula (5) can be carried out at a temperature between 20° and 120° C. It is advantageous to maintain anhydrous conditions. An excess of the acid halide can be used as the reaction medium but it is also possible to add a solvent which is inert under the reaction conditions.

Examples of solvents which can be used are: cycloaliphatic or aromatic hydrocarbons, such as, for example, cyclohexane, benzene, toluene or xylene; chlorinated hydrocarbons, such as chloroform, carbon tetrachloride, ethylene chloride or chlorobenzenes; and ethers, such as dioxane, diethyl ether, glycol dimethyl ether or tetrahydrofurane.

The concentration of the reactants is not critical; however, it is advantageous to use one mol equivalent of each of the reactants. The manufacturing process is as a rule carried out by adding all of the reactants, that is to say the compound of the formula (4), the compound of the formula (5) and the acid halide, together at the same time. However, it is also possible to employ a procedure in which the indole compound of the formula (4) and the acid halide are first allowed to react and the compound of the formula (5) is then added. The end product of the formula (1) is isolated in a generally known manner, for example by pouring the reaction mixture into ice water, the acids being buffered, if necessary, with an alkaline compound, for example alkali metal hydroxides or alkali metal carbonates, filtering off the precipitate formed and washing and drying, as well as, optionally, by chromatography or recrystallisation of the product. Liquid end products can be obtained by extraction with suitable organic solvents and optionally purified by distillation.

A further embodiment for the manufacture of the new compounds of the formula (1) consists in reacting a carbinol compound of the general formula

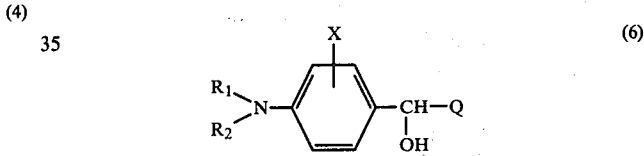

(6)

in which $R_1$, $R_2$, X and Q have the indicated meaning, with a 2-(2'-hydroxyphenyl)-indole compound of the general formula (4) and oxidising the reaction product to a compound of the formula (1).

The reaction of the carbinol compounds of the formula (6) with the indole compound of the formula (4) gives a reaction product of the formula

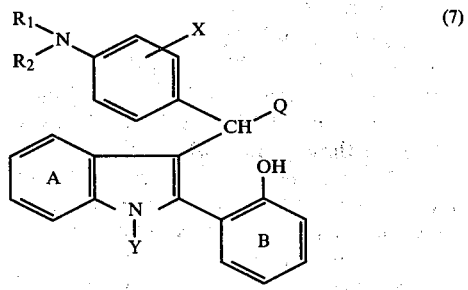

(7)

in which A, B, $R_1$, $R_2$, X, Y and Q have the indicated meaning, water being eliminated.

This condensation reaction is appropriately carried out in a polar organic solvent, especially in lower aliphatic alcohols, such as, for example, methanol, ethanol or isopropanol, or in ethers, such as, for example, tetrahydrofurane, and preferably in the presence of an acid catalyst. The reaction can already be carried out at room temperature (20° to 25° C.) However, it is appropriate to use elevated temperature, preferably 40° to 100° C. Examples of suitable acid catalysts are lower aliphatic carboxylic acids, such as formic acid or acetic acid, and inorganic acids, such as hydrochloric acid, sulphuric acid, phosphoric acid or perchloric acid. The reaction time depends on the temperature and as a rule is between ½ hour and 15 hours.

The resulting reaction product of the formula (7) can be isolated if desired.

The oxidation of the reaction product of the formula (7) to the chromenoindole compounds of the formula (1) is effected with oxidising agents. Examples of suitable oxidising agents are chromates, bichromates, chlorates, chlorites, peroxides, manganese dioxide, lead dioxide, chlorine, bromine, molecular oxygen, air, perborates, permanganates and, in particular, hydrogen peroxide.

The reaction is advantageously carried out in the presence of an organic solvent which does not participate in the oxidation. Suitable solvents are again lower aliphatic alcohols, such as ethanol and isopropanol, ethylene glycol monomethyl ether or ethylene glycol monoethyl ether or lower aliphatic ketones, such as acetone, methyl ethyl ketone or methyl isobutyl ketone.

The best results, in respect of yield and purity of the resulting chromenoindole compounds, are achieved with hydrogen peroxide as the preferred oxidising agent and this is preferably used in ethanol or isopropanol. For this purpose, the reaction mixture is advantageously rendered alkaline after the condensation reaction of the starting materials of the formulae (6) and (4) has ended. Alkalis such as alkali metal hydroxides, for example sodium hydroxide or potassium hydroxide, alkali metal carbonates or alkali metal bicarbonates, ammonia, alkali metal alcoholates, such as sodium methylate or potassium methylate or sodium ethylate or potassium ethylate, as well as mixtures of these compounds, are suitable for rendering the reaction mixture alkaline. Preferably, the pH value is adjusted to 8 to 13.

The oxidation temperature as a rule depends on the oxidising agent and, above all, on the boiling point of the solvent used. It is appropriately between 20° and 100° C. When hydrogen peroxide is used, the oxidation preferably proceeds at between 60° and 90° C. The oxidation as a rule takes 1 to 5 hours.

The starting materials of the formula (4) are as a rule manufactured according to the instructions of A. Calvaire and R. Pallaud, Compt. rend. 250 (1960), 3194–95 by reacting a o-hydroxy-acetophenone of the formula

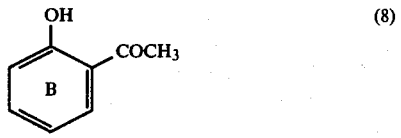

with a phenylhydrazine of the formula

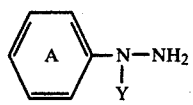

in which A, B and Y have the indicated meaning, and converting the resulting phenylhydrazone into the desired 2-(2'-hydroxyphenyl)-indole compound by heating in a suitable cyclising agent, for example polyphosphoric acid.

When phosphoric acid is used as the cyclising agent, the compounds of the formula (4) can be obtained direct without isolation of the phenylhydrazone which is formed as an intermediate product.

The chromenoindole compounds of the formulae (1) to (3) are usually colourless or slightly coloured. When these colour-forming agents are brought into contact with an acid developer, that is to say an electron acceptor, they give intense red to blue colour shades which are outstandingly fast to light. They are therefore also very valuable as a mixture with one or more other known colour-forming agents, for example 3,3-(bis-aminophenyl)-phthalides, 3,3-(bis-indolyl)-phthalides, 2,6-diaminofluoranes or benzoylleucomethylene blue, in order to give blue, navy blue, grey or black colorations.

The new colour-forming agents exhibit an improved colour intensity and fastness to light both on clay and on phenolic substrates. They are suitable, above all, for use in a pressure-sensitive or heat-sensitive recording material, which can be either copying material or documenting material.

A pressure-sensitive material comprises, for example, at least one pair of sheets which contain at least one colour-forming agent of the formulae (1) to (3), dissolved in an organic solvent, and a solid electron acceptor as the developer. The colour-forming agent gives a coloured marking at the points at which it comes into contact with the electron acceptor.

Typical examples of such developers are attapulgite clay, silton clay, silicon dioxide, bentonite, halloysite, aluminium oxide, aluminium sulphate, aluminium phosphate, zinc chloride, kaolin or any desired acid clay or organic compounds having an acid reaction, such as, for example, optionally ring-substituted phenols, salicyclic acid or salicylates and their metal salts, and also a polymeric material having an acid reaction, such as, for example, a phenolic polymer, an alkylphenol-acetylene resin, a maleic acid/rosin resin or a partially or completely hydrolysed polymer of maleic anhydride with styrene, ethylene, vinyl methyl ether or carboxypolymethylene. Preferred developers are attapulgite clay, silton clay or a phenol-formaldehyde resin.

These electron acceptors are preferably applied in the form of a layer to the front of the receiving sheet.

In order to prevent the colour-forming agents becoming prematurely active in the pressure-sensitive recording material, these agents are as a rule separated from the electron acceptor. This can appropriately be achieved by incorporating the colour-forming agents into foam-like, sponge-like or honeycombed structures. Preferably, the colour-forming agents are enclosed in micro-capsules, which as a rule can be crushed by pressure.

When the capsules are crushed by pressure, for example by means of a pencil, and the solution of the colour-forming agent is thus transferred onto an adjacent sheet which is coated with an electron acceptor, a coloured area is produced. This colour results from the dyestuff, formed during this process, which absorbs in the visible region of the electromagnetic spectrum.

The colour-forming agents are preferably encapsulated in the form of solutions in organic solvents. Examples of suitable solvents are preferably non-volatile solvents, for example polyhalogenated diphenyl, such as trichlorodiphenyl, or a mixture thereof with liquid paraffin, and also tricresyl phosphate, di-n-butyl phthalate, dioctyl phthalate, trichlorobenzene, nitrobenzene, trichloroethyl phosphate, petroleum ether, hydrocarbon oils, such as paraffin, alkylated derivatives of diphenyl, naphthalene or triphenyl, terphenyls, partially hydrogenated terphenyl or other chlorinated or hydrogenated, fused, aromatic hydrocarbons.

The capsule walls can be formed uniformly around the droplets of the solution of the colour-forming agent by means of coacervation forces, and the encapsulating material can consist, for example, of gelatine and gum arabic, as described, for example, U.S. Pat. No. 2,800,457. The capsules can preferably also be formed from an aminoplast or modified aminoplasts by polycondensation, as described in British Patent Specification Nos. 989,264 and 1,156,725.

The micro-capsules containing the colour-forming agents of the formula (1) can be used for the manufacture of pressure-sensitive copying materials of the most diverse known types. The various systems differ from one another essentially in the arrangement of the capsules and of the colour reactants and in the carrier material.

A preferred arrangement is that in which the encapsulated colour-forming agent is applied in the form of a layer to the back of a transfer sheet and the electron acceptor is applied in the form of a layer to the front of a receiving sheet. However, the components can also be used in the paper pulp.

Another arrangement of the components is for the microcapsules containing the colour-forming agents and the developer to be in or on the same sheet, in the form of one or more individual layers, or in the paper pulp.

Pressure-sensitive copying materials of this type are described, for example, in U.S. Pat. Nos. 2,730,457, 2,932,582, 3,418,250, 3,418,656, 3,427,180 and 3,516,846. Further systems are described in British Pat. Specifications Nos. 1,042,596, 1,042,597, 1,042,598, 1,042,599, 1,053,935 and 1,517,650. Micro-capsules which contain the colour-forming agents of the formula (1) are suitable for each of these systems and also for other pressure-sensitive systems.

The capsules are preferably secured to the carrier by means of a suitable adhesive. Since paper is the preferred carrier material, these adhesives are in the main paper-coating agents, such as gum arabic, polyvinyl alcohol, hydroxymethylcellulose, casein, methylcellulose or dextrin.

The term "paper" used here includes not only normal papers of cellulose fibres but also papers in which the cellulose fibres are replaced (partially or completely) by fibres of synthetic polymers.

The chromenoindole compounds of the formulae (1) to (3) can also be used as colour-forming agents in a thermo-reactive recording material. This recording material as a rule contains at least one carrier, a colour-forming agent, a solid electron acceptor and, if appropriate, also a binder. Thermo-reactive recording systems include, for example, heat-sensitive recording and copying materials and papers. These systems are used, for example, for recording information, for example in computers, teleprinters or telex machines, or in measuring instruments. The production of the image (production of the marking) can also be effected manually with a heated pen. Laser beams are a further device for producing markings by means of heat.

The thermo-reactive recording material can be built up in such a way that the colour-forming agent is dissolved or dispersed in a layer of binder and the developer is dissolved or dispersed in the binder in a second layer. Another possibility is for both the colour-forming agent and the developer to be dispersed in one layer. The binder is softened by means of heat in specific areas and at these points, at which heat is applied, the colour-forming agent comes into contact with the electron acceptor and the desired colour develops immediately.

Suitable developers are the same electron acceptors as are used in pressure-sensitive papers. Examples of developers are the acid clay minerals and phenolic resins already mentioned, or also phenolic compounds such as, for example, 4-tert.-butylphenol, 4-phenylphenol, 4-hydroxydiphenyl ether, α-naphthol, β-naphthol, methyl 4-hydroxybenzoate, 4-hydroxyacetophenone, 2,2'-dihydroxydiphenyl, 4,4'-isopropylidenediphenol, 4,4'-isopropylidene-bis-(2-methylphenol), 4,4'-bis-(hydroxyphenyl)-valeric acid, hydroquinone, pyrogallol, phloroglucinol, p-, m- and o-hydroxybenzoic acid, gallic acid, 1-hydroxy-2-naphthoic acid and also boric acid and organic acids such as aliphatic dicarboxylic acids, such as, for example, tartaric acid, oxalic acid, maleic acid, citric acid, citraconic acid or succinic acid.

Film-forming binders which can be melted are preferably used to manufacture the thermo-reactive recording material. These binders are usually soluble in water, whilst the chromenoindole compounds and the developer are insoluble in water. The binder should be capable of dispersing and fixing the colour-forming agent and the developer at room temperature.

The binder softens or melts under the action of heat, so that the colour-forming agent comes into contact with the developer and can form a colour. Examples of binders which are soluble in water or at least swellable in water are hydrophilic polymers, such as polyvinyl alcohol, polyacrylic acid, hydroxyethylcellulose, methylcellulose, carboxymethylcellulose, polyacrylamide, polyvinylpyrrolidone, gelatine and starch.

When the colour-forming agent and the developer are present in two separate layers, binders which are insoluble in water, that is to say binders which are soluble in non-polar or only slightly polar solvents, such as, for example, natural rubber, synthetic rubber, chlorinated rubber, alkyd resins, polystyrene, styrene/butadiene copolymers, polymethyl methacrylates, ethylcellulose, nitrocellulose and polyvinylcarbazole, can be used. However, the peferred arrangement is that in which the colour-forming agent and the developer are contained in a water-soluble binder in one layer.

The thermo-reactive layers can contain further additives. In order to improve the whiteness, to facilitate printing of the papers and to prevent the heated pen from adhering, these layers can contain, for example, talc, $TiO_2$, $ZnO$ or $CaCO_3$, or also organic pigments, such as, for example, urea-formaldehyde polymers. In order to ensure that the colour is formed only within a limited temperature range, substances such as urea, thiourea, acetanilide, phthalic anhydride or other corresponding fusible products which induce simultaneous melting of the colour-forming agent and the developer, can be added.

In the examples which follow, the percentages quoted relate to weight, unless otherwise indicated.

EXAMPLE 1

21 g (0.1 mol) of 2-(2'-hydroxyphenyl)-indole and 27 g (0.1 mol) of bis-(4,4'-dimethylamino)-benzophenone are stirred in 100 ml of phosphorus oxychloride for 5 hours under reflux. The reaction mixture is poured onto ice and rendered alkaline with sodium hydroxide. The resulting precipitate is then filtered off and chromatographed over 2,500 g of silica gel using a mixture of benzene and ethyl acetate in a ratio of 9:1. The first fraction is crystallised from methanol with the addition of a little dilute ammonia. This gives 29 g of 6,6-bis-(4-dimethylaminophenyl)-6H-chromeno[4,3-b]-indole of the formula

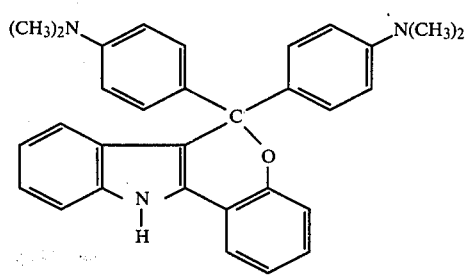

in the form of white crystals with a melting point of 145°–150° C. (decomposition). On silton clay, this colour-forming agent develops a blue colour with a λ max of 620 nm.

EXAMPLE 2

If, in Example 1, the 2-(2'-hydroxyphenyl)-indole is replaced by 22.3 g of 2-(2'-hydroxy-5'-methyl-phenyl)-indole and in other respects the procedure followed is as described in Example 1, 19.2 g of a compound of the formula

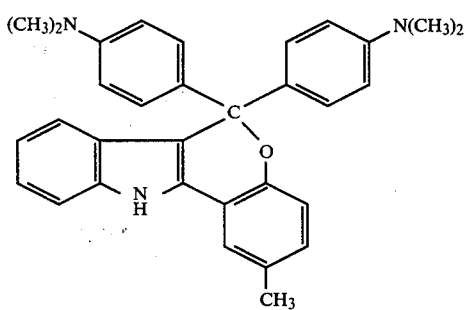

are obtained. This compound melts at 151°–155° C. (decomposition). On silton clay, it develops a blue colour with a λ max of 615 nm.

EXAMPLE 3

If, in Example 1, the 2-(2'-hydroxyphenyl)-indole is replaced by 24.4 g of 2-(2'-hydroxy-5'-chlorophenyl)-indole and in other respects the procedure followed is as described in Example 1, 25.3 g of a compound of the formula

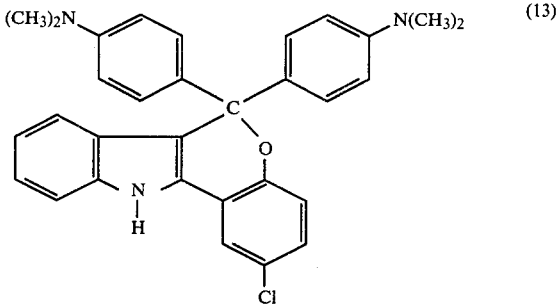

are obtained. This compound melts at 165°–170° C. (decomposition) and on silton clay develops a blue colour with a λ max of 620 nm.

EXAMPLE 4

11.26 g of 4-dimethylaminobenzophenone and 10.5 g of 2-(2'-hydroxyphenyl)-indole are stirred in 50 ml of phosphorus oxychloride for 4 hours under reflux. The reaction mixture is poured onto ice and rendered alkaline with ammonia and the resulting precipitate is then filtered off. Repeated dissolving of the residue in methanol with the addition of a little 37% strength hydrochloric acid and precipitating with ammonia and water gives a slightly impure product, which is purified through a column, packed with 80 g of silica gel/ethyl acetate. Crystallisation from ethyl acetate/ethanol gives 16.7 g of 6-phenyl-6-(4-dimethylaminophenyl)-6H-chromeno[4,3-b]-indole of the formula

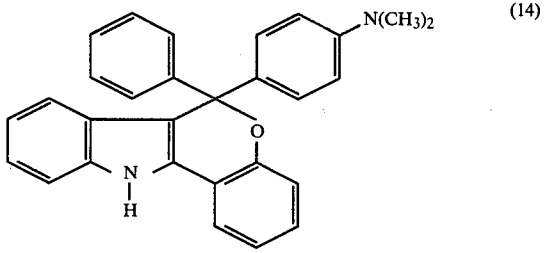

in the form of yellowish crystals with a melting point of 229°–231° C. On silton clay, this colour-forming agent develops a blue colour with a λ max of 600 nm.

EXAMPLE 5

Production of a pressure-sensitive copying paper

A solution of 3 g of the chromenoindole compound of the formula (11) in 97 g of partially hydrogenated terphenyl is emulsified in a solution of 12 g of pigskin gelatine in 88 g of water at 50° C. A solution of 12 g of gum arabic in 88 g of water at 50° C. is then added and thereafter 200 ml of water at 50° C. are added. The resulting emulsion is poured into 600 g of ice water and the mixture is cooled and by this means coacervation is effected. A sheet of paper is coated with the suspension of the micro-capsules which is thus obtained, and dried. A second sheet of paper is coated with silton clay. The first sheet and the paper coated with silton clay are placed on top of one another with the coatings adjacent to one another.

Pressure is exerted by writing by hand or with a typewriter on the first sheet and an intense blue copy, which is outstandingly fast to light, develops on the sheet coated with clay.

Corresponding blue shade effects can be achieved by using each of the other colour-forming agents of the formulae (12) to (14) indicated in the examples.

EXAMPLE 6

Production of a thermo-reactive paper 6 g of an aqueous dispersion which contains 1.57% of the chromenoindole compound of the formula (12) and 6.7% of polyvinyl alcohol are mixed with 134 g of an aqueous dispersion which contains 14% of 4,4-isopropylidenediphenol, 8% of attapulgite clay and 6% of polyvinyl alcohol. This mixture is applied to a paper and dried. An intense blue colour, which is outstandingly fast to light, is obtained by bringing the paper into contact with a heated ballpoint pen.

Corresponding blue shade effects can be achieved by using each of the other colour-forming agents of the formulae (11), (13) and (14) indicated in the examples.

We claim:

1. A pressure-sensitive or heat-sensitive recording material which contains a colour former system comprising, as the colour-forming agent, at least one chromenoindole compound of the formula

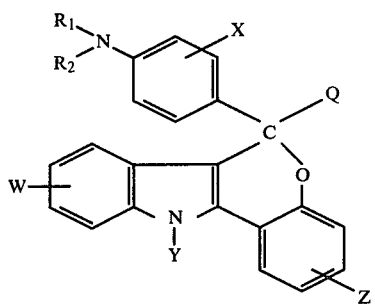

wherein $R_1$ and $R_2$ independently of one another represent lower alkyl, phenyl or benzyl, and $R_1$ also represents hydrogen, or $R_1$ and $R_2$, together with the nitrogen atom which links them, represent pyrrolidino, piperidino or morpholino, X represents hydrogen, halogen, methyl or lower alkoxy, Q represents hydrogen, lower alkyl, phenyl, benzyl or the group of the formula

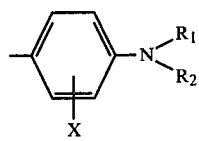

W represents hydrogen, halogen, lower alkyl, lower alkoxy or phenoxy, Y represents hydrogen, lower alkyl, phenyl or benzyl and Z represents hydrogen, halogen, lower alkyl, lower alkoxy, amino or amino substituted by lower alkyl, benzyl or phenyl.

2. A pressure-sensitive or heat-sensitive recording material of claim 1, which contains at least one chromenoindole compound of the formula

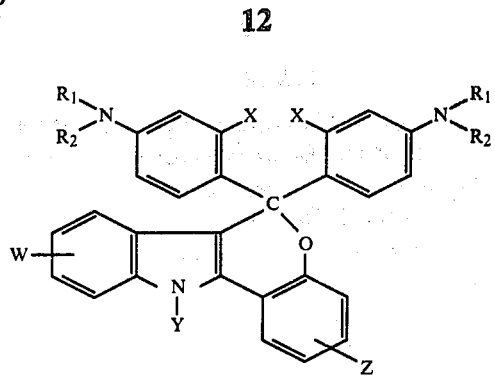

wherein $R_1$ and $R_2$ independently of one another represent lower alkyl or benzyl, W represents hydrogen, chlorine, methyl or methoxy, X represents hydrogen, methyl, methoxy or ethoxy, Y represents hydrogen, lower alkyl, benzyl or phenyl and Z represents hydrogen, chlorine, methyl, methoxy or amino monosubstituted or disubstituted by lower alkyl.

3. A pressure-sensitive or heat-sensitive recording material of claim 1, which contains at least one chromenoindole compound of the formula indicated in claim 1, wherein $R_1$ and $R_2$ represents methyl or ethyl, X represents hydrogen, methyl or ethoxy, W and Z each represent hydrogen and Y represents hydrogen, methyl or ethyl.

4. A pressure-sensitive or heat-sensitive recording material of claim 1, which contains a chormenoindole of the formula

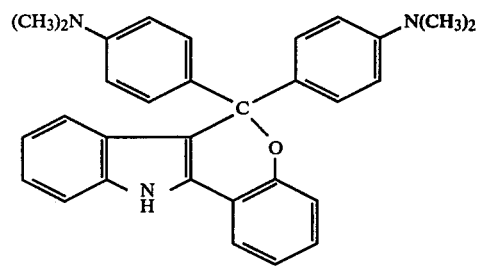

5. A pressure-sensitive or heat-sensitive recording material of claim 1, which contains a chromenoindole of the formula

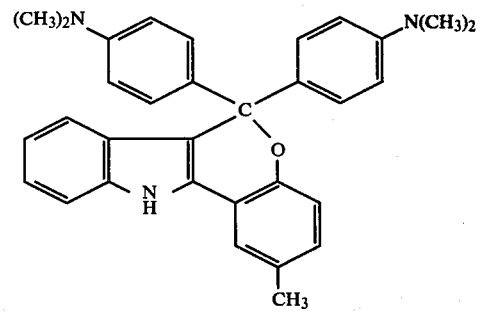

6. A pressure-sensitive or heat-sensitive recording material of claim 1, which contains a chromenoindole of the formula

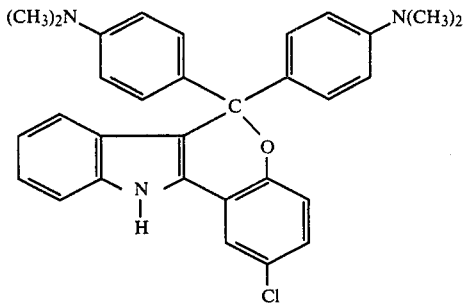

7. A pressure-sensitive recording material according to claim 1, wherein the colour former system comprises at least one chromenoindole compound of the formula indicated in claim 1, as the colour-forming agent, dissolved in an organic solvent, and at least one solid electron acceptor.

8. A pressure-sensitive recording material according to claim 7, wherein the chromenoindole compound is encapsulated in micro-capsules.

9. A pressure-sensitive recording material according to claim 7, wherein the solid electron acceptor is attapulgite clay, silton clay or a phenol-formaldehyde resin.

10. A pressure-sensitive recording material according to claim 8, wherein the encapsulated chromenoindole compound is applied in the form of a layer to the back of a transfer sheet and the electron acceptor is applied in the form of a layer to the face of a receiving sheet.

11. A pressure-sensitive recording material according to claim 1, which contains the chromenoindole compound together with one or more other colour-forming agents.

12. A heat-sensitive recording material according to claim 1, which contains in at least one layer, at least one said colour-forming agent, at least one solid electron acceptor and, where appropriate, at least one binder.

13. A heat-sensitive recording material according to claim 12, which contains at least one chromenoindole compound as the colour-forming agent and at least one electron acceptor in at least one binder layer on paper.

14. A heat-sensitive recording material according to claim 12, wherein the electron acceptor is attapulgite clay, silton clay, a phenolic compound, a phenolic resin or a solid organic acid.

* * * * *